US008304387B2

(12) United States Patent
Treuheit et al.

(10) Patent No.: US 8,304,387 B2
(45) Date of Patent: Nov. 6, 2012

(54) THERAPEUTIC FORMULATIONS OF KERATINOCYTE GROWTH FACTOR

(75) Inventors: Michael J. Treuheit, Newbury Park, CA (US); Vasumathi Dharmavaram, Encino, CA (US); Judith Purtell, Calabasas, CA (US); Suzanne E. Roy, Agoura, CA (US)

(73) Assignee: Swedish Orphan Biovitrum AB (publ), Stockholm (SE)

( * ) Notice: Subject to any disclaimer, the term of this patent is extended or adjusted under 35 U.S.C. 154(b) by 94 days.

(21) Appl. No.: 11/302,033

(22) Filed: Dec. 12, 2005

(65) Prior Publication Data
US 2006/0128622 A1 Jun. 15, 2006

Related U.S. Application Data

(60) Provisional application No. 60/636,210, filed on Dec. 15, 2004.

(51) Int. Cl.
*A61K 38/18* (2006.01)
*A61K 38/00* (2006.01)
*A61P 1/04* (2006.01)
*A61P 17/02* (2006.01)

(52) U.S. Cl. ....... 514/9.2; 514/13.2; 514/18.6; 530/324; 530/350

(58) Field of Classification Search .................. None
See application file for complete search history.

(56) References Cited

U.S. PATENT DOCUMENTS

| | | | |
|---|---|---|---|
| 5,580,856 A * | 12/1996 | Prestrelski et al. | 514/21 |
| 5,654,405 A | 8/1997 | Rubin et al. | |
| 5,665,870 A | 9/1997 | Rubin et al. | |
| 5,677,278 A | 10/1997 | Gospodarowicz et al. | |
| 5,707,805 A | 1/1998 | Rubin et al. | |
| 5,731,170 A | 3/1998 | Rubin et al. | |
| 5,741,642 A | 4/1998 | Rubin et al. | |
| 5,773,586 A | 6/1998 | Gospodarowicz et al. | |
| 5,843,883 A | 12/1998 | Gospodarowicz et al. | |
| 5,863,767 A | 1/1999 | Gospodarowicz et al. | |
| 6,008,328 A | 12/1999 | Hsu et al. | |
| 6,074,848 A | 6/2000 | Gospodarowicz et al. | |
| 6,238,888 B1 * | 5/2001 | Gentz et al. | 435/69.4 |
| 6,420,531 B1 | 7/2002 | Rubin et al. | |
| 6,677,301 B1 * | 1/2004 | Gospodarowicz et al. | 514/2 |
| 6,709,842 B1 | 3/2004 | Rubin et al. | |
| 6,833,132 B1 | 12/2004 | Rubin et al. | |
| 7,026,291 B1 | 4/2006 | Rubin et al. | |
| 7,084,119 B2 | 8/2006 | Gospodarowicz et al. | |
| 7,138,114 B2 * | 11/2006 | Kendrick et al. | 424/94.67 |
| 7,247,452 B2 | 7/2007 | Gospodarowicz et al. | |
| 2002/0012961 A1 * | 1/2002 | Botstein et al. | 435/69.1 |
| 2006/0128622 A1 | 6/2006 | Treuheit et al. | |

FOREIGN PATENT DOCUMENTS

| WO | WO 90/08771 | 8/1990 | |
|---|---|---|---|
| WO | WO9312812 | * | 7/1993 |
| WO | WO 96/11949 | | 4/1996 |
| WO | WO 96/11951 | | 4/1996 |
| WO | WO 98/24813 | | 6/1998 |
| WO | WO9932135 | * | 7/1999 |

OTHER PUBLICATIONS

Accession No. NP_002000 (GI:4503705), Fibroblast Growth Factor 7 Precursor [*Homo sapiens*], GenPept Database, National Center for Biotechnology Information, Release Date Dec. 31, 2006.

Accession No. NM_002009 (GI:15147344), *Homo sapiens* Fibroblast Growth Factor 7 (Keratinocyte Growth Factor) (FGF7), mRNA, GenBank Database, National Center for Biotechnology Information, Release Date Dec. 31, 2006.

Alarid, E. T. et al., "Keratinocyte Growth Factor Functions in Epithelial Induction During Seminal Vesicle Development", *Proceedings of the National Academy of Science, U.S.A.*, 91:1074-1078 (1994).

Bosch, A., et al., "Proliferation Induced by Keratinocyte Growth Factor Enhances in Vivo Retroviral-Mediated Gene Transfer to Mouse Hepatocytes", *Journal of Clinical Investigation*, 98(12):2683-2687 (1996).

Carpenter, J. F., et al., "Interactions of Stabilizing Additives with Proteins During Freeze-Thawing and Freeze-Drying", *Develop. Biol. Standard* 74:225-239 (1991).

Chang, B. S., et al., "Surface-Induced Denaturation of Proteins During Freezing and its Inhibition by Surfactants", *Journal of Pharmaceutical Sciences*, 85(12):1325-1330 (1996).

Chen, T., "Formulation Concerns of Protein Drugs", *Drug Development and Industrial Pharmacy*, 18(11&12):1311-1354 (1992).

Danilenko D. M., et al., "Keratinocyte Growth Factor is an Important Endogenous Mediator of Hair Follicle Growth, Development, and Differentiation (*Normalization of the* Nu/Nu *Follicular Differentiation Defect and Amelioration of Chemotherapy-Induced Alopecia*)", *American Journal of Pathology* 147:145-154, (1995).

Danilenko D. M., "Preclinical and Early Clinical Development of Keratinocyte Growth Factor, an Epithelial-Specific Tissue Growth Factor", *Toxicologic Pathology*, 27(1):64-71 (1999).

Finch P. W., et al., "Human KGF is FGF-Related with Properties of a Paracrine Effector of Epithelial Cell Growth", *Science*, 245:752-755 (1989).

Gospodarowicz, D., et al., "Comparison of the Ability of Basic and Acidic Fibroblast Growth Factor to Stimulate the Proliferation of an Established Keratinocyte Cell Line: Modulation of Their Biological Effects by Heparin, Transforming Growth Factor β (TGFβ), and Epidermal Growth Factor (EGF)", *Journal of Cellular Physiology*, 142:325-333 (1990).

Housley R. M., et al., "Keratinocyte Growth Factor Induces Proliferation of Hepatocytes and Epithelial Cells Throughout the Rat Gastrointestinal Tract", *Journal of Clinical Investigation*, 94:1764-1777 (1994).

Hsu, Y., et al., "Heparin is Essential for a Single Keratinocyte Growth Factor Molecule to Bind and Form a Complex with Two Molecules of the Extracellular Domain of its Receptor", *Biochemistry*, 38:2523-2534 (1999).

(Continued)

*Primary Examiner* — Xiaozhen Xie

(74) *Attorney, Agent, or Firm* — Fish & Richardson P.C.

(57) ABSTRACT

The present invention provides long-term stable formulations of lyophilized keratinocyte growth factor and methods for making a lyophilized composition comprising keratinocyte growth factor.

20 Claims, 3 Drawing Sheets

OTHER PUBLICATIONS

Kaza, A. K., et al., "Keratinocyte Growth Factor Enhances Post-Pneumonectomy Lung Growth by Alveolar Proliferation", *Circulation*, 106 (Suppl. I):I-120-1-124 (2002).

Mackenzie, A. P., "Non-Equilibrium Freezing Behaviour of Aqueous Systems", *Philosophical Transactions of the Royal Society of London*, 278:167-189 (1977).

T. Maniatis et. al., "Molecular Cloning—A Laboratory Manual", Cold Spring Harbor Laboratory (1982), pp. 387 to 389.

Marchese, C., et al., "Human Keratinocyte Growth Factor Activity on Proliferation and Differentiation of Human Keratinocytes: Differentiation Response Distinguishes KGF from EGF Family", *Journal of Cellular Physiology*, 144:326-332 (1990).

Meropol, N. J., et al., "Randomized Phase I Trial of Recombinant Human Keratinocyte Growth Factor Plus Chemotherapy: Potential Role as Mucosal Protectant", *Journal of Clinical Oncology*, 21(8):1452-1458 (2003).

Mitchell, J. R., et al., "Acetaminophen-Induced Hepatic Necrosis. I. Role of Drug Metabolism", *The J. of Pharm. and Experimental Therapeutics*, 187(1):185-194 (1973).

Moore J. V., "Clonogenic Response of Cells of Murine Intestinal Crypts to 12 Cytotoxic Drugs", *Cancer Chemotherapy and Pharmacology*, 15:11-15 (1985).

Nguyen, H. Q., et al., "Expression of Keratinocyte Growth Factor in Embryonic Liver of Transgenic Mice Causes Changes in Epithelial Growth and Differentiation Resulting in Polycystic Kidneys and Other Organ Malformations", *Oncogene*, 12:2109-2119 (1996).

Panos, R. J., et al., "Keratinocyte Growth Factor and Hepatocyte Growth Factor/Scatter Factor are Heparin-Binding Growth Factors for Alveolar Type II Cells in Fibroblast-Conditioned Medium", *The Journal of Clinical Investigation*, 92:969-977 (1993).

Panoskaltsis-Mortari, A., et al., "Keratinocyte Growth Factor Facilitates Alloengraftment and Ameliorates Graft-Versus-Host Disease in Mice by a Mechanism Independent of Repair of Conditioning-Induced Tissue Injury", *Blood*, 96(13):4350-4356 (2000).

Pierce, G. F., et al., "Stimulation of All Epithelial Elements During Skin Regeneration by Keratinocyte Growth Factor", *Journal of Exp. Medicine*, 179:831-840 (1994).

Playford, R. J., et al., "Effects of Keratinocyte Growth Factor (KGF) on Gut Growth and Repair", *Journal of Pathology*, 184:316-322, (1998).

Porter R. M., "Mouse Models for Human Hair Loss Disorders" *Journal of Anat*. 202:125-131 (2003).

Rubin, J. S., et al., "Purification nd Characterization of a Newly Identified Growth Factor Specific for Epithelial Cells", *Proceedings of the National Academy of Science, U.S.A.*, 86:802-806 (1989)a.

Simonet, S. W., et al., "Pulmonary Malformation in Transgenic Mice Expressing Human Keratinocyte Growth Factor in the Lung", *Proceedings of the National Academy of Science, U.S.A.*, 92:12461-12465, (1995).

Sonis, S. T., et al., "An Animal Model for Mucositis Induced by Cancer Chemotherapy", *Oral Surgery Oral Medicine Oral Pathology*, 69:437-443 (1990).

Spielberger, R. et al., "Palifermin for Oral Mucositis after Intensive Therapy for Hematologic Cancers", *The New England Journal of Medicine*, 351:2590-2598 (2004).

Staiano-Coico, L., et al., "Human Keratinocyte Growth Factor Effects in a Porcine Model of Epidermal Wound Healing", *The Journal of Experimental Medicine*, 178:865-878 (1993).

Stolk, J., et al., "Induction of Emphysema and Bronchial Mucus Cell Hyperplasia by Intratracheal Instillation of Lipopolysaccharide in the Hamster." *Journal of Pathology* 167:349-56 (1992).

Tang, et al., "Design of Freeze-Drying Processes for Pharmaceuticals: Practical Advice", *Pharmaceutical Research*, 21(2):191-200, (2004).

Thakore, K. N. et al., "Role of Hepatocellular Regeneration in $CCl_4$ Autoprotection", *Toxicologic Pathology*, 19(1):47-58 (1991).

Tomaszewski, K.E., et al., "The Production of Hepatic Cirrhosis in Rats", *Journal of Applied Toxicology*, 11(3):229-231 (1991).

Ulich, T. R., et al., "Keratinocyte Growth Factor is a Growth Factor for Mammary Epithelium *In Vivo* (*The Mammary Epithelium of Lactating Rats is Resistant to the Proliverative Action of Keratinocyte Growth Factor*)", *American Journal of Pathology*, 144:862-868 (1994).

Ulich, T. R., et al., "Keratinocyte Growth Factor is a Growth Factor for Type II Pneumocytes In Vivo", *Journal of Clinical Investigation*, 93:1298-1306, (1994).

Werner, S., et al., "The Function of KGF in Morphogenesis of Epithelium and Reepithelialization of Wounds", *Science*, 266:819-822 (1994).

Withers H. R., et al., "Microcolony Survival Assay for Cells of Mouse Intestinal Mucosa Exposed to Radiation", *Int. J. Radiat.*, 17(3):261-267 (1970).

Yi, E. S., et al., "Keratinocyte Growth Factor Induces Pancreatic Ductal Epithelial Proliferation", *American Journal of Pathology*, 145(1):80-85 (1994).

Yi, E. S., et al., "Keratinocyte Growth Factor Causes Proliferation of Urothelium In Vivo", *The Journal of Urology*, 154:1566-1570 (1995).

Yi, E. S., et al., "Keratinocyte Growth Factor Decreases Pulomonary Edema, Transforming Growth Factor-Beta and Platelet-Derived Growth Factor-BB Expression, and Alveolar Type II Cell Loss in Bleomycin-Induced Lung Injury", *Inflammation*, 22:315-325 (1998).

Zhang, M. Z. et al., "A new Strategy for Enhancing the Stability of Lyophilized Protein: The Effect of the Reconstitution Medium on Keratinocyte Growth factor", *Pharmaceutical Research* 12:1447-1452 (1995).

\* cited by examiner

FIG. 2A
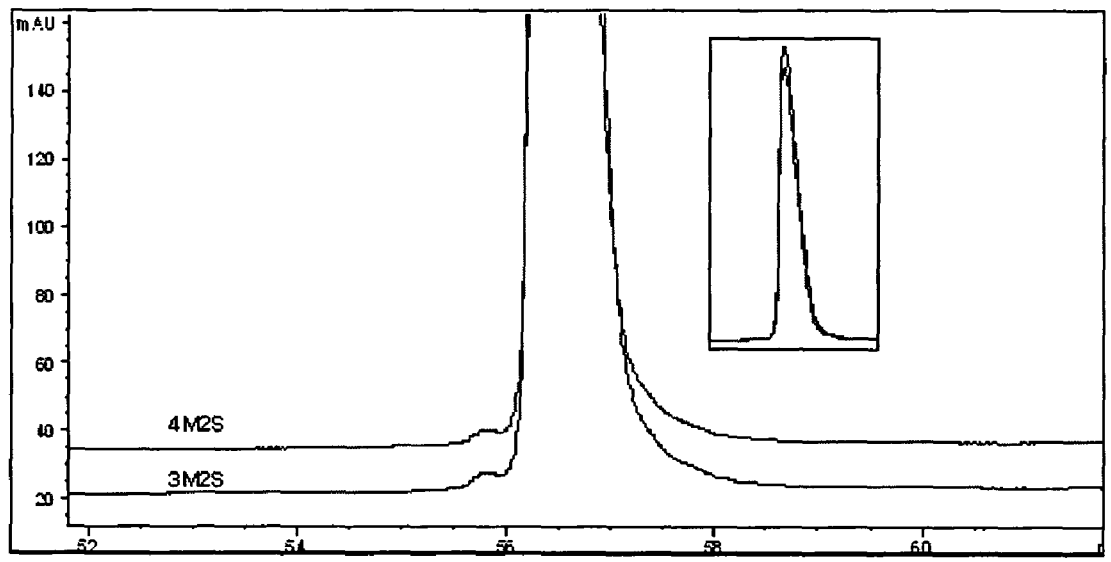
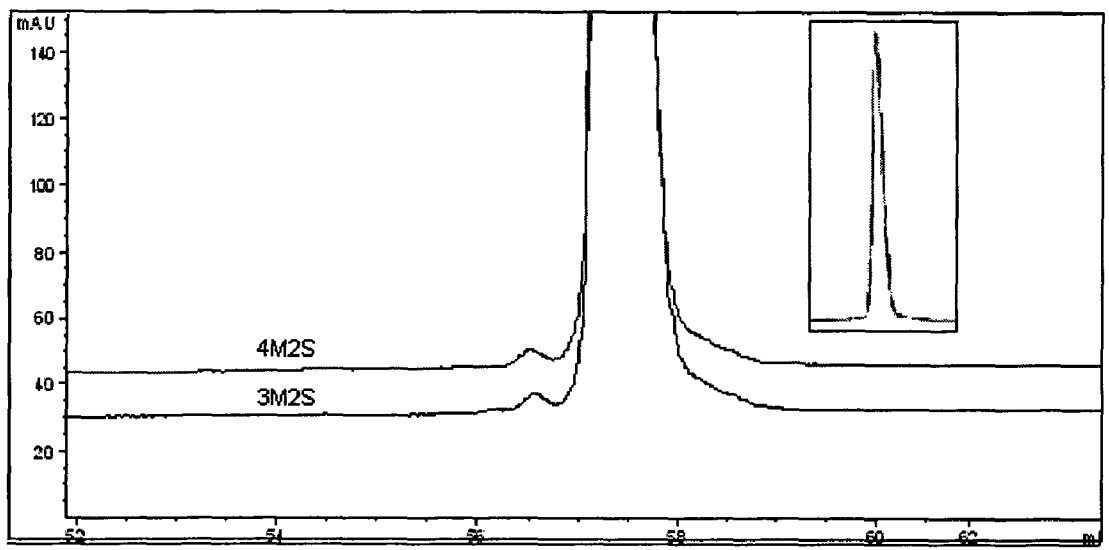
FIG. 2B

SEQUENCE LISTING

<160> NUMBER OF SEQ ID NOS: 3

<210> SEQ ID NO 1
<211> LENGTH: 3853
<212> TYPE: DNA
<213> ORGANISM: homo sapiens
<220> FEATURE:
<221> NAME/KEY: CDS
<222> LOCATION: (446)..(1030)

<400> SEQUENCE: 1

```
acgcgctcac acacagagag aaaatccttc tgcctgttga tttatggaaa caattatgat      60
tctgctggag aacttttcag ctgagaaata gtttgtagct acagtagaaa ggctcaagtt     120
gcaccaggca gacaacagac atggaattct tatatatcca gctgttagca acaaaacaaa     180
agtcaaatag caaacagcgt cacagcaact gaacttacta cgaactgttt ttatgaggat     240
ttatcaacag agttatttaa ggaggaatcc tgtgttgtta tcaggaacta aaaggataag     300
gctaacaatt tggaaagagc aactactctt tcttaaatca atctacaatt cacagatagg     360
aagaggtcaa tgacctagga gtaacaatca actcaagatt cattttcatt atgttattca     420
tgaacacccg gagcactaca ctata atg cac aaa tgg ata ctg aca tgg atc      472
                            Met His Lys Trp Ile Leu Thr Trp Ile
                             1               5 ctg cca act ttg ctc tac aga tca tgc ttt cac att atc tgt cta gtg      520
Leu Pro Thr Leu Leu Tyr Arg Ser Cys Phe His Ile Ile Cys Leu Val
 10              15                  20                  25 ggt act ata tct tta gct tgc aat gac atg act cca gag caa atg gct      568
Gly Thr Ile Ser Leu Ala Cys Asn Asp Met Thr Pro Glu Gln Met Ala
             30                  35                  40 aca aat gtg aac tgt tcc agc cct gag cga cac aca aga agt tat gat      616
Thr Asn Val Asn Cys Ser Ser Pro Glu Arg His Thr Arg Ser Tyr Asp
         45                  50                  55 tac atg gaa gga ggg gat ata aga gtg aga aga ctc ttc tgt cga aca      664
Tyr Met Glu Gly Gly Asp Ile Arg Val Arg Arg Leu Phe Cys Arg Thr
     60                  65                  70 cag tgg tac ctg agg atc gat aaa aga ggc aaa gta aaa ggg acc caa      712
Gln Trp Tyr Leu Arg Ile Asp Lys Arg Gly Lys Val Lys Gly Thr Gln
 75                  80                  85 gag atg aag aat aat tac aat atc atg gaa atc agg aca gtg gca gtt      760
Glu Met Lys Asn Asn Tyr Asn Ile Met Glu Ile Arg Thr Val Ala Val
 90                  95                 100                 105 gga att gtg gca atc aaa ggg gtg gaa agt gaa ttc tat ctt gca atg      808
Gly Ile Val Ala Ile Lys Gly Val Glu Ser Glu Phe Tyr Leu Ala Met
             110                 115                 120 aac aag gaa gga aaa ctc tat gca aag aaa gaa tgc aat gaa gat tgt      856
Asn Lys Glu Gly Lys Leu Tyr Ala Lys Lys Glu Cys Asn Glu Asp Cys
         125                 130                 135 aac ttc aaa gaa cta att ctg gaa aac cat tac aac aca tat gca tca      904
Asn Phe Lys Glu Leu Ile Leu Glu Asn His Tyr Asn Thr Tyr Ala Ser
     140                 145                 150 gct aaa tgg aca cac aac gga ggg gaa atg ttt gtt gcc tta aat caa      952
Ala Lys Trp Thr His Asn Gly Gly Glu Met Phe Val Ala Leu Asn Gln
 155                 160                 165
```

-continued

| | |
|---|---|
| aag ggg att cct gta aga gga aaa aaa acg aag aaa gaa caa aaa aca<br>Lys Gly Ile Pro Val Arg Gly Lys Lys Thr Lys Lys Glu Gln Lys Thr<br>170                    175                    180                    185 | 1000 |
| gcc cac ttt ctt cct atg gca ata act taa ttgcatatgg tatataaaga<br>Ala His Phe Leu Pro Met Ala Ile Thr<br>                    190 | 1050 |
| acccagttcc agcagggaga tttctttaag tggactgttt tctttcttct caaaattttc | 1110 |
| tttcctttta ttttttagta atcaagaaag gctggaaaaa ctactgaaaa actgatcaag | 1170 |
| ctggacttgt gcatttatgt ttgttttaag acactgcatt aaagaaagat ttgaaaagta | 1230 |
| tacacaaaaa tcagatttag taactaaagg ttgtaaaaaa ttgtaaaact ggttgtacaa | 1290 |
| tcatgatgtt agtaacagta attttttttct taaattaatt taccccttaag agtatgttag | 1350 |
| atttgattat ctgataatga ttatttaaat attcctatct gcttataaaa tggctgctat | 1410 |
| aataataata atacagatgt tgttatataa ggtatatcag acctacaggc ttctggcagg | 1470 |
| atttgtcaga taatcaagcc acactaacta tggaaaatga gcagcatttt aaatgctttc | 1530 |
| tagtgaaaaa ttataatcta cttaaactct aatcagaaaa aaaattctca aaaaaactat | 1590 |
| tatgaaagtc aataaaatag ataatttaac aaaagtacag gattagaaca tgcttatacc | 1650 |
| tataaataag aacaaaattt ctaatgctgc tcaagtggaa agggtattgc taaaaggatg | 1710 |
| tttccaaaaa tcttgtatat aagatagcaa cagtgattga tgataatact gtacttcatc | 1770 |
| ttacttgcca caaaataaca ttttataaat cctcaaagta aaattgagaa atctttaagt | 1830 |
| tttttttcaag taacataatc tatctttgta taattcatat ttgggaatat ggcttttaat | 1890 |
| aatgttcttc ccacaaataa tcatgctttt ttcctatggt tacagcatta aactctattt | 1950 |
| taagttgttt ttgaacttta ttgttttgtt atttaagttt atgttatttta taaaaaaaaa | 2010 |
| accttaataa gctgtatctg tttcatatgc ttttaatttt aaaggaataa caaaactgtc | 2070 |
| tggctcaacg gcaagtttcc ctccctttttc tgactgacac taagtctagc acacagcact | 2130 |
| tgggccagca atcctggaa gcagacaaaa ataagagcct gaagcaatgc ttacaataga | 2190 |
| tgtctcacac agaacaatac aaatatgtaa aaactctttc accacatatt cttgccaatt | 2250 |
| aattggatca tataagtaaa atcattacaa atataagtat ttacaggatt ttaaagttag | 2310 |
| aatatatttg aatgcatggg tagaaaatat catattttaa aactatgtat atttaaattt | 2370 |
| agtaattttc taatctctag aaatctctgc tgttcaaaag gtggcagcac tgaaagttgt | 2430 |
| tttcctgtta gatggcaaga gcacaatgcc caaaatagaa gatgcagtta agaataaggg | 2490 |
| gccctgaatg tcatgaaggc ttgaggtcag cctacagata acaggattat tacaaggatg | 2550 |
| aatttccact tcaaaagtct ttcattggca gatcttggta gcactttata tgttcaccaa | 2610 |
| tgggaggtca atatttatct aatttaaaag gtatgctaac cactgtggtt ttaatttcaa | 2670 |
| aatatttgtc attcaagtcc ctttacataa atagtatttg gtaatacatt tatagatgag | 2730 |
| agttatatga aaaggctagg tcaacaaaaa caatagattc atttaatttt cctgtggttg | 2790 |
| acctatacga ccaggatgta gaaaactaga agaactgcc cttcctcaga tatactcttg | 2850 |
| ggagagagca tgaatggtat tctgaactat cacctgattc aaggactttg ctagctaggt | 2910 |
| tttgaggtca ggcttcagta actgtagtct tgtgagcata ttgagggcag aggaggactt | 2970 |
| agttttttcat atgtgtttcc ttagtgccta gcagactatc tgttcataat cagttttcag | 3030 |
| tgtgaattca ctgaatgttt atagacaaaa gaaaatacac actaaaacta atcttcattt | 3090 |
| taaaagggta aaacatgact atacagaaat ttaaatagaa atagtgtata tacatataaa | 3150 |
| atacaagcta tgttaggacc aaatgctctt tgtctatgga gttatacttc catcaaatta | 3210 |

```
catagcaatg ctgaattagg caaaaccaac atttagtggt aaatccattc ctggtagtat    3270
aagtcaccta aaaaagactt ctagaaatat gtactttaat tatttgtttt tctcctattt    3330
ttaaatttat tatgcaaatt ttagaaaata aaatttgctc tagttacaca cctttagaat    3390
tctagaatat taaaactgta aggggcctcc atccctctta ctcatttgta gtctaggaaa    3450
ttgagatttt gatacaccta aggtcacgca gctgggtaga tatacagctg tcacaagagt    3510
ctagatcagt tagcacatgc tttctactct tcgattatta gtattattag ctaatggtct    3570
ttggcatgtt tttgttttt  atttctgttg agatatagcc tttacatttg tacacaaatg    3630
tgactatgtc ttggcaatgc acttcataca caatgactaa tctatactgt gatgatttga    3690
ctcaaaagga gaaagaaat  tatgtagttt tcaattctga ttcctattca ccttttgttt    3750
atgaatggaa agctttgtgc aaaatataca tataagcaga gtaagccttt taaaaatgtt    3810
ctttgaaaga taaaattaaa tacatgagtt tctaacaatt aga                      3853
```

<210> SEQ ID NO 2  
<211> LENGTH: 194  
<212> TYPE: PRT  
<213> ORGANISM: homo sapiens  
<220> FEATURE:  
<221> NAME/KEY: MISC_FEATURE  
<222> LOCATION: (1)..(31)  
<223> OTHER INFORMATION: signal peptide

<400> SEQUENCE: 2

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr
```

<210> SEQ ID NO 3  
<211> LENGTH: 140  
<212> TYPE: PRT  
<213> ORGANISM: homo sapiens

<400> SEQUENCE: 3

```
Ser Tyr Asp Tyr Met Glu Gly Gly Asp Ile Arg Val Arg Arg Leu Phe
1               5                   10                  15

Cys Arg Thr Gln Trp Tyr Leu Arg Ile Asp Lys Arg Gly Lys Val Lys
            20                  25                  30

Gly Thr Gln Glu Met Lys Asn Asn Tyr Asn Ile Met Glu Ile Arg Thr
        35                  40                  45

Val Ala Val Gly Ile Val Ala Ile Lys Gly Val Glu Ser Glu Phe Tyr
    50                  55                  60

Leu Ala Met Asn Lys Glu Gly Lys Leu Tyr Ala Lys Lys Glu Cys Asn
65                  70                  75                  80

Glu Asp Cys Asn Phe Lys Glu Leu Ile Leu Glu Asn His Tyr Asn Thr
                85                  90                  95

Tyr Ala Ser Ala Lys Trp Thr His Asn Gly Gly Glu Met Phe Val Ala
            100                 105                 110

Leu Asn Gln Lys Gly Ile Pro Val Arg Gly Lys Lys Thr Lys Lys Glu
            115                 120                 125

Gln Lys Thr Ala His Phe Leu Pro Met Ala Ile Thr
        130                 135                 140
```

THERAPEUTIC FORMULATIONS OF KERATINOCYTE GROWTH FACTOR

This application claims the benefit of U.S. Provisional Application No. 60/636,210, filed Dec. 15, 2004, which is hereby incorporated by reference.

FIELD OF THE INVENTION

The present invention relates to formulations of lyophilized keratinocyte growth factor and methods for making a lyophilized composition comprising keratinocyte growth factor.

BACKGROUND OF THE INVENTION

Keratinocyte growth factor (KGF) is a growth factor specific for epithelial cells that was first identified in conditioned medium of a human embryonic lung fibroblast cell line [Rubin et al., *Proc. Natl. Acad. Sci. USA* 86:802-806 (1989)]. Expression of messenger RNA for KGF has been detected in several stromal fibroblast cell lines derived from epithelial tissues at various stages of development. The transcript for KGF was also evident in RNA extracted from normal adult kidney and organs of the gastrointestinal tract [Finch et al., *Science* 245:752-755 (1989)]. Evidence that KGF is secreted from fibroblasts in culture and is expressed in vivo in the dermis but not the epidermis indicates that KGF may be an important normal paracrine effector of keratinocyte proliferation. Studies have shown that KGF is as potent as epidermal growth factor (EGF) in stimulating the proliferation of primary or secondary human keratinocytes in tissue culture [Marchese et al., *J. Cell. Phys.* 144:326-332 (1990)]. KGF is produced by mesenchymal cells near the epithelium of many organs including the epidermis, oral and lower gastrointestinal epithelium, pancreas, liver, lung, urothelium, prostate epithelium and others [Finch et al, supra, Housley et al., *J Clin Invest.* 94:1764-77, (1994); Yi et al., *Am J Path.* 145:80-85, (1994); Pierce et al., *J Exp. Med.* 179831-40, (1994); Yi et al, *J Urol.* 154:1566-70, (1995); and Ulich et al., *J Clin Invest.* 93:1298-1306, (1994)].

The purification of KGF from conditioned medium of a human embryonic fibroblast cell line, as well as the partial amino acid sequencing of purified KGF, the cloning of the KGF gene, and the expression of the gene in bacterial cells to yield biologically active recombinant KGF are described in International Patent Publication WO 90/08771. This publication also discloses that KGF or KGF-like polypeptides are useful as wound healing agents for burn wounds or to stimulate transplanted corneal tissue.

Ex vivo and in vivo studies in normal adult animals have shown that KGF-1 (hereinafter "KGF") produces changes in hair follicle morphogenesis, hepatocyte proliferation, and epithelial cell proliferation in the lung, breast, pancreas, stomach, small intestine, and large intestine [Panos et al., *J. Clin. Invest.* 92:969-977 (1993); Ulich et al., *Am. J. Path.* 144:862-868 (1994); Yi et al., *Am. J. Path.* 145:80-85 (1994); and Ulich et al., *J. Clin. Invest.* 93:1298-1306 (1994)]. The role of KGF in embryonic or neonatal development is currently under investigation; however, KGF has been documented to be an important mediator of seminal vesicle development in the newborn mouse [Alarid et al., *Proc. Natl. Acad. Sci. USA* 91:1074-1078 (1994)]. Additionally, mice overexpressing KGF in hepatocytes exhibit polycystic kidneys [Nguyen et al., *Oncogene* 12:2109-19, (1996)], while KGF overexpresion in lung using a surfactant promoter result in mice with pulmonary cystadenomas [Simonet et al., *Proc. Natl. Acad. Sci. USA* 92:12461-65, (1995)], demonstrating the importance of KGF in normal renal and pulmonary development.

KGF has been demonstrated to increase re-epithelialization and increased thickness of the epithelium when recombinant KGF was topically applied to wounds surgically induced in the rabbit ear or in porcine skin [Pierce et al., *J. Exp. Med.* 179:831-840 (1994]); and Staiano-Coico et al., *J. Exp. Med.* 178:865-878 (1993)]. Bosch, et al., [*J. Clin. Invest.* 98:2683-2687 (1996)] reported that administration of keratinocyte growth factor will induce the proliferation of liver cells.

Typically, purified polypeptides are only marginally stable in an aqueous state and undergo chemical and physical degradation resulting in a loss of biological activity during processing and storage. Additionally, polypeptide compositions in aqueous solution undergo hydrolysis, such as deamidation and peptide bond cleavage. These effects represent a serious problem for therapeutically active polypeptides which are intended to be administered to humans within a defined dosage range based on biological activity.

Administration of purified keratinocyte growth factor remains a promising candidate to treat many diseases that affect the human population. However, the ability of the KGF to remain a stable pharmaceutical composition over time in a variety of storage conditions and then be effective for patients in vivo has not been addressed. Thus, there remains a need in the art to provide keratinocyte growth factor in stable formulations that are useful as therapeutic agents to treat the variety of diseases which benefit from KGF-mediated stimulation of epithelial cell growth.

SUMMARY OF THE INVENTION

The present invention provides a novel formulation useful for lyophilization of keratinocyte growth factor (KGF), resulting in a highly stable KGF product. The stable KGF product is useful as a therapeutic agent in the treatment of individuals suffering from disorders or conditions that can benefit from the administration of KGF.

In one aspect, the invention provides a lyophilized keratinocyte growth factor composition comprising histidine, a bulking agent, a surfactant, and a sugar, such as a stabilizing suger.

In one embodiment, the KGF composition comprises the amino acid sequence of SEQ ID NO:2 or variant thereof. A variant of KGF proteins include allelic variations, or deletion(s), substitution(s) or insertion(s) of amino acids, including fragments, chimeric or hybrid molecules of native KGF. For example, the invention contemplates that the KGF is ΔN23 KGF (SEQ ID NO:3), wherein the first 23 amino acids of the native KGF are deleted. Variants include those molecules described herein, such as charge-change polypeptides wherein one or more of amino acid residues 41-154 of native KGF (SEQ ID NO:2) are deleted or substituted with a neutral residue or negatively charged residue selected to effect a protein with a reduced positive charge. A still further example of KGF includes, but is not limited to, proteins generated by substituting at least one amino acid having a higher loop-forming potential for at least one amino acid within a loop-forming region of $Asn^{115}$-$His^{116}$-$Tyr^{117}$-$Asn^{118}$-$Thr^{119}$ of native KGF. A still further example includes proteins having one or more amino acid substitutions, deletions or additions within a region of amino acids 123-133 (amino acids 154-164 of SEQ ID NO:2) of native KGF.

In one aspect, the invention contemplates use of a bulking agent/osmolarity regulating agent. Bulking agents may be either crystalline (for example, glycine, mannitol) or amorphous (for example, L-histidine, sucrose, polymers such as dextran, polyvinylpyrolidone, carboxymethylcellulose, and lactose). In one embodiment, the bulking agent is mannitol. In a further embodiment, the mannitol is incorporated at a concentration of about 2% to about 5% w/v. In a yet further embodiment, the concentration is about 3% to about 4.5% w/v. In another embodiment, the mannitol is at a concentration of 4% w/v.

In another aspect, the invention provides for a composition comprising a stabilizing sugar. Sugars contemplated for use include but are not limited to, sucrose, trehalose or glycine. In one embodiment, the sugar is sucrose. In a related embodiment, the sucrose is at a concentration of about 1-3% w/v. In a further embodiment, the sucrose is at a concentration of 2%.

It is contemplated that the composition of the invention is adjusted to a pH in a range of about 5.0 to about 8.0. In one embodiment, the KGF composition has a pH in the range of about 6.0 to about 8.0. In another embodiment, the composition has a pH in a range of about 6.0 to about 7.0. In a further embodiment, the composition has a pH of about 6.5.

In a further aspect, the composition contemplates use of a surfactant. It is contemplated that the surfactant used includes, but is not limited to, polysorbate 20 or polysorbate 80. In one embodiment, the surfactant is polysorbate 20. In a related embodiment, the polysorbate 20 concentration is within a range of about 0.1% to about 0.004% w/v. In a further embodiment, the polysorbate 20 concentration is about 0.01% w/v.

In one aspect, the invention contemplates a lyophilized keratinocyte growth factor composition comprising 10 mM histidine, 4% mannitol, 2% sucrose, and 0.01% polysorbate 20, wherein the composition is at a pH of 6.5.

The invention further provides a method for making a lyophilized keratinocyte growth factor comprising the steps of: a) preparing a solution of histidine, a bulking agent, a stabilizing sugar; and surfactant; and b) lyophilizing said KGF. In a related aspect, the invention contemplates a method for making a lyophilized keratinocyte growth factor further comprising, prior to the lyophilization step: b) adjusting the pH of the solution to a pH between about 6.0 and about 8.0; c) preparing a solution containing a keratinocyte growth factor; d) buffer exchanging the solution of step (c) into the solution of step (b); e) adding an appropriate amount of a surfactant, and f) lyophilizing the mixture from step (e). It is further contemplated that the KGF may be a KGF protein set out in SEQ ID NO:2, SEQ ID NO:3 or variants thereof.

In one aspect, the method of the invention contemplates use of a bulking agent/osmolarity regulating agent, wherein the bulking agents may be either crystalline (for example, glycine, mannitol) or amorphous (for example, L-histidine, sucrose, polymers such as dextran, polyvinylpyrolidone, carboxymethylcellulose, and lactose). In one embodiment, the bulking agent is mannitol. In another embodiment, the mannitol is at a concentration of about 2% to about 5% w/v. In a related embodiment, the mannitol is at a concentration of about 3% to about 4.5% w/v. In a further embodiment, the mannitol is at a concentration of 4% w/v.

In another aspect, the method of invention provides for a composition comprising a sugar, wherein the sugar is a stabilizing sugar. Sugars contemplated for use in the method include but are not limited to, sucrose, trehalose or glycine. In one embodiment, the sugar is sucrose. In a related embodiment, the sucrose is at a concentration of about 1% to about 3% w/v. In a further embodiment, the sucrose is at a concentration of 2%.

It is contemplated in the methods of the invention that the pH is adjusted to physiological pH. In one embodiment, the pH is adjusted to a range of about 5.0 to about 8.0. In another embodiment, the pH is adjusted to a range of about 6.0 to about 8.0. In a further embodiment, the pH is adjusted to a range of about 6.0 to about 7.0. In a still further embodiment, the pH is adjusted to a pH value of 6.5.

In a further aspect, the methods of the invention contemplate use of a surfactant. It is contemplated that the surfactant used includes, but is not limited to, polysorbate 20 or polysorbate 80. In one embodiment, the surfactant is polysorbate 20. In a related embodiment, the polysorbate 20 concentration is within a range of about 0.1% to about 0.004% w/v. In a further embodiment, the polysorbate 20 concentration is about 0.01% w/v.

In one aspect, the invention contemplates a method for making a lyophilized keratinocyte growth factor composition comprising 10 mM histidine, 4% mannitol, 2% sucrose, and 0.01% (w/v) polysorbate 20, wherein the composition is at a pH of about 6.5.

The invention further contemplates a method for treating a disease by increasing KGF-mediated stimulation of epithelial cell growth comprising administering to a subject an effective amount of a lyophilized keratinocyte growth factor composition of the invention.

It is contemplated that the disease to be treated is gut toxicity; mucositis; a burn or other partial and full thickness injuries; repopulation of hair follicles, sweat glands, and sebaceous glands; adnexal structure proliferation; epidermolysis bullosa; chemotherapy-induced alopecia; male-pattern baldness; gastric ulcers; duodenal ulcers; erosive gastritis, esophagitis, or esophageal reflux; inflammatory bowel disease; hyaline membrane disease; injuries from smoke inhalation; emphysema; hepatic cirrhosis, liver failure, acute viral hepatitis, other toxic insults to the liver; or graft-versus-host disease (GVHD).

Also contemplated by the invention is a kit for preparing an aqueous pharmaceutical composition comprising a first container having a lyophilized keratinocyte growth factor composition, and a second container having a physiologically acceptable reconstitution solution for the lyophilized composition. It is contemplated that the KGF protein is set out in SEQ ID NO:2, SEQ ID NO:3, or variants thereof. The physiologically acceptable reconstitution solution may be any pharmaceutically acceptable carrier or diluent, including, but not limited to, any and all clinically useful solvents, dispersion media, coatings, antibacterial and antifungal agents, isotonic and absorption delaying agents and the like, including those agents disclosed herein. Additionally, the KGF composition may be administered to a subject by any route deemed appropriate by the treating physician, including orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well.

BRIEF DESCRIPTION OF THE DRAWINGS

FIG. 2 depicts reversed-phase (RP)HPLC chromatograms comparing KGF formulations lyophlilized in 10 mM histidine, 0.01% polysorbate 20, and either 4% mannitol/2% sucrose or 3% mannitol/2% sucrose. FIG. 2A depicts time zero after lyophilization while FIG. 2B shows product after storage for 1 year at 4° C. Inset shows the area around the main peak.

DETAILED DESCRIPTION OF THE INVENTION

Figure 1:
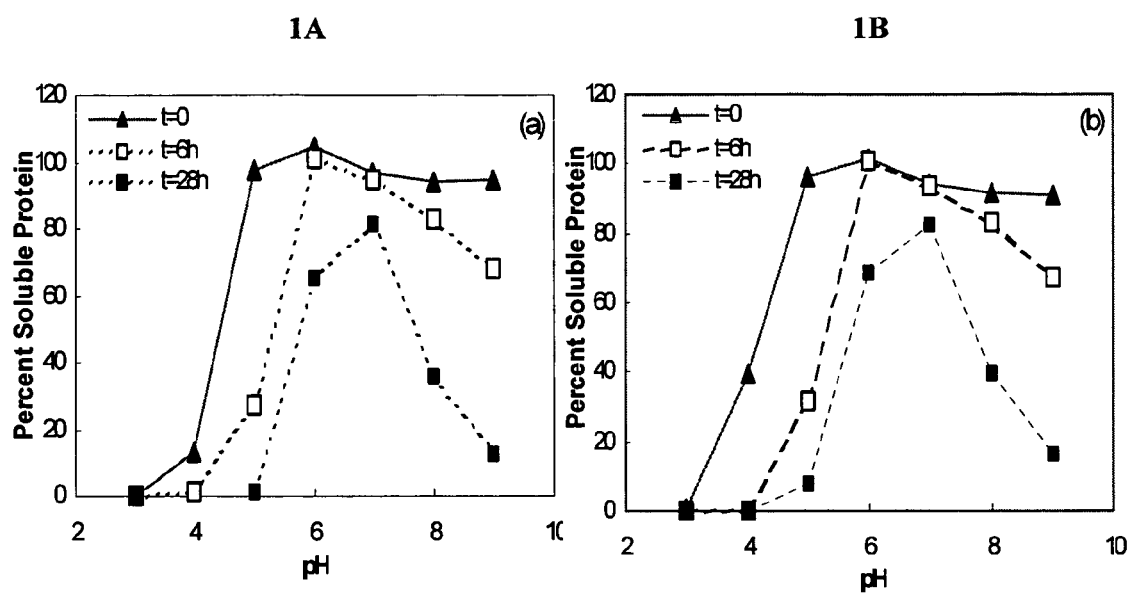
FIG. 1 depicts Size-exclusion (SE)-HPLC (FIG. 1A) and Cation-exchange (CE)-HPLC (FIG. 1B) analysis of soluble protein in liquid KGF formulations at differing pH.

The present invention relates to formulations for lyophilization of purified keratinocyte growth factor which provide a stable protein product and increase the shelf life of the purified protein. The invention further provides a method for making a lyophilized composition comprising keratinocyte growth factor.

As used herein, "keratinocyte growth factor" or "KGF" refers to the keratinocyte growth factor polynucleotide (SEQ ID NO:1, Genbank Accession No. NM_002009) or polypeptide as set forth in SEQ ID NO:2 (Genbank Accession No. NP_002000) or an analog thereof, or alternatively an active fragment of keratinocyte growth factor or an analog thereof, such as ΔN23 KGF (SEQ ID NO:3), or a factor that binds and activates the keratinocyte growth factor receptor. In a preferred embodiment, KGF is ΔN23 KGF, a recombinantly produced form of KGF in which the first 23 amino acids of the amino-terminus have been deleted from the mature KGF (no signal sequence attached). See, e.g., U.S. Pat. Nos. 5,677,278; 6,677,301, 6,074,848, 5,843,883, 5,863,767 and 5,773,586, all assigned to CHIRON Corp., U.S. Pat. No. 5,731,170, and PCT Application No. WO 90/08771, published Aug. 9, 1990 (directed to full length forms of KGF and variants); and PCT Application No. WO 96/11949, published Apr. 25, 1996; PCT Application No. WO 96/11951, published Apr. 25, 1996; and PCT Application No. WO 98/24813, published Jun. 11, 1998 (directed to stable analogs of KGF) all of which are incorporated herein by reference in their entirety, including figures.

KGF analogs having increased stability over natural KGF are described in PCT International Publication WO 96/11951 and U.S. Pat. No. 6,677,301, and such KGF analogs are contemplated by the invention. Alternatively, any fragment of the entire KGF polypeptide or analog thereof which retains complete or even partial KGF activity is contemplated.

It should be understood that the terms "keratinocyte growth factor" and "KGF" as employed in this description are intended to include, and to mean interchangeably unless otherwise indicated, native KGF and KGF analog proteins (or "muteins") characterized by a peptide sequence substantially the same as all or part of the peptide sequence of native KGF and by retaining some or all of the biological activity of native KGF, particularly non-fibroblast epithelial cell proliferation, e.g., exhibiting at least about 500-fold greater stimulation of BALB/MK keratinocyte cells than that of NIH/3T3 fibroblast cells, and at least about 50-fold greater stimulation of BALB/MK keratinocyte cells than for BS/589 epithelial cells or for CC1208 epithelial cells, as determined by H-thymidine incorporation. Also contemplated by the invention are peptides "characterized by a peptide sequence substantially the same as the peptide sequence of native KGF" which refers to a peptide sequence which is encoded by a DNA sequence capable of hybridizing with the coding region of SEQ ID NO:1, under moderately to highly stringent hybridization conditions as exemplified herein.

Stringent conditions, in the hybridization context, will be stringent combined conditions of salt, temperature, organic solvents and other parameters typically controlled in hybridization reactions. Exemplary stringent hybridization conditions are hybridization in 4×SSC at 62°-67° C., followed by washing in 0.1×SSC at 62°-67° C. for approximately an hour. Alternatively, exemplary stringent hybridization conditions are hybridization in 45-55% formamide, 4×SSC at 40°-45° C. [See, T. Maniatis et. al., *Molecular Cloning (A Laboratory Manual)*; Cold Spring Harbor Laboratory (1982), pages 387 to 389.]

KGF proteins include allelic variations, or deletion(s), substitution(s) or insertion(s) of amino acids, including fragments, chimeric or hybrid molecules of native KGF. A preferred KGF molecule of this invention is ΔN23 KGF. Other examples of KGF include, without limitation, proteins having residues corresponding to $Cys^1$ and $Cys^{15}$ of SEQ ID NO:2 replaced or deleted, with the resultant molecule having improved stability as compared with the parent molecule (as taught in commonly owned U.S. Pat. No. 6,008,328). Another example of KGF includes, but is not limited to, charge-change polypeptides wherein one or more of amino acid residues 41-154 of native KGF (preferably residues $Arg^{41}$, $Gln^{43}$, $Lys^{55}$, $Lys^{95}$, $Lys^{128}$, $Asn^{137}$, $Gln^{138}$, $Lys^{139}$, $Arg^{144}$, $Lys^{147}$, $Gln^{152}$, $Lys^{153}$ or $Thr^{154}$) are deleted or substituted with a neutral residue or negatively charged residue selected to effect a protein with a reduced positive charge. A still further example of KGF includes, but is not limited to, proteins generated by substituting at least one amino acid having a higher loop-forming potential for at least one amino acid within a loop-forming region of $Asn^{115}$-$His^{116}$-$Tyr^{117}$-$Asn^{118}$-$Thr^{119}$ of native KGF (as taught in U.S. Pat. No. 6,008,328). A still further example includes proteins having one or more amino acid substitutions, deletions or additions within a region of amino acids 123-133 (amino acids 154-164 of SEQ ID NO:2) of native KGF.

Specifically contemplated KGF proteins include the following KGF molecules (referred to by the residue found at that position in the mature protein (minus signal sequence) set forth in SEQ ID NO:2, followed by that amino acid position in parentheses and then either the substituted residue or "–" to designate a deletion): ΔN15, ΔN16, ΔN18, ΔN23, ΔN24, ΔN25, ΔN26, or ΔN27 KGF, C(1,15)S, ΔN15-ΔN24, ΔN3/C(15)S, ΔN3/C(15)-, ΔN8/C(15)S, ΔN8/C(15)-, C(1,15)S/R(144)E, C(1,15)S/R(144)Q, ΔN23/R(144)Q, C(1,15,40)S, C(1,15,102)S, C(1,15,102,106)S, ΔN23/N(137)E, ΔN23/K(139)E, ΔN23/K(139)Q, ΔN23/R(144)A, ΔN23/R(144)E, ΔN23/R(144)L, ΔN23/K(147)E, ΔN23/K(147)Q, ΔN23/K(153)E, ΔN23/K(153)Q, ΔN23/Q(152)E/K(153)E; R(144)Q and H(116)G.

KGF's proliferative effects on many different types of epithelial and endothelial cells implicate it as a useful therapeutic in treatment of many conditions or diseases affecting an individual. The following is a description of diseases and medical conditions which can be treated with KGF of the invention.

Gut toxicity is a major limiting factor in radiation and chemotherapy treatment regimes. Pretreatment with KGF may have a cytoprotective effect on the small intestinal mucosa, allowing increased dosages of such therapies while reducing potential fatal side effects of gut toxicity. Recent phase I clinical trials of patients administered recombinant human KGF before treatment with the chemotherapeutic agent 5-fluorouracil suggest that treatment with KGF will promote decreased incidence of mucositis [Meropol et al., *J Clin Oncol.* 21:1452-8 (2003)] Standard in vivo models of radiation-induced gut toxicity which permit the predictive testing of compounds having human therapeutic efficacy are well-known [Withers and Elkind, "Microcolony Survival Assay for Cells of Mouse Intestinal Mucosa Exposed to Radiation", *Int. J. Radiat.,* 17:261-267 (1970). Standard in vivo models of chemotherapy-induced gut toxicity which are predictive of human therapeutic efficacy are well-known. Sonis, et al., "An Animal Model for Mucositis Induced by Cancer Chemotherapy, Oral Surg.", *Oral Med. Oral Pathol.,* 69:437-431 (1990); and Moore, "Clonogenic Response of Cells of Murine Intestinal Crypts to 12 Cytotoxic Drugs", *Cancer Chemotherapy Pharmacol.,* 15:11-15 (1985)].

KGF treatment has a striking effect on the production of mucus throughout the gastrointenstinal tract. This property may be useful in protecting the gut mucosa from injurious substances that are ingested, or in limiting the spread of injury in conditions such as inflammatory bowel diseases.

Stimulation of proliferation and differentiation of adnexal structures such as hair follicles, sweat glands, and sebaceous glands is of critical importance in regenerating epidermis and dermis in patients with burns and other partial and full thickness injuries. At present, surface defects heal by scar formation and keratinocyte resurfacing; full regeneration of skin is not yet possible. Repopulation of hair follicles, sweat glands, and sebaceous glands does not occur presently in full thickness skin defects, including burns. The use of KGF can enable such repopulation. Standard in vivo models of adnexal structure proliferation and stimulation which permit the predictive testing of compounds having human therapeutic efficacy for burns and other partial and full-thickness injuries are well-known [Mustoe, et al., "Growth factor-induced acceleration of tissue repair through direct and inductive activities in a rabbit dermal ulcer model" *J. Clin. Invest.,* 87:694-703 (1991); Pierce, et al., "Platelet-derived growth factor (BB homodimer), transforming growth factor-beta 1, and basic fibroblast growth factor in dermal wound healing. Neovessel and matrix formation and cessation of repair" *Am. J. Path.* 140:1375-88 (1992); and Davis, et al., "Second-degree burn healing: the effect of occlusive dressings and a cream." *J. of Surgical Res.* 48:245-248 (1990)].

Epidermolysis bullosa is a defect in adherence of the epidermis to the underlying dermis, resulting in frequent open, painful blisters which can cause severe morbidity. Accelerated re-epithelialization of these lesions, such as by treatment with KGF, would result in less risk of infection, diminished pain, and less wound care.

Chemotherapy-induced alopecia results when patients are treated with courses of chemotherapy for malignancy. At present no therapeutics are effective at preventing the hair follicle cells from death, which cause the transient loss of hair. KGF provides such a means. Standard in vivo models of chemotherapy-induced alopecia which permit the predictive testing of compounds having human therapeutic efficacy are well-known. [Sawada, et al., "Cyclosporin A Stimulates Hair Growth in Nude Mice", *Laboratory Investigation,* 56(6):684 (1987); Holland, "Animal Models of Alopecia", *Clin. Dermatol,* 6:159:162 (1988); Hussein, "Protection from Chemotherapy-induced Alopecia in a Rat Model", *Science,* 249: 1564-1566 (1990); and Hussein, et al., "Interleukin 1 Protects against 1-B-D-Arabinofuranosyulcytosine-induced Alopecia in the Newborn Rat Animal Model", *Cancer Research,* 51:3329-3330 (1991)].

Male-pattern baldness is prevalent and essentially untreatable. The progressive loss of hair in men and women is a serious cosmetic problem. KGF deficient mice exhibit ruffled unkempt coat while KGF receptor knockouts exhibited thin skin, low numbers of hair follicles, and delayed wound healing [Werner et al., *Science* 266:819-22 (1994)]. In experimental models of alopecia, pre-treatment with recombinant KGF protected against approximately 50% of the alopecia induced by administration of the chemotherapeutic agent cytosine arabinoside (ARA-c) [Danilenko et al., *Am J Path.* 147:145-54, (1995)]. These conditions could be treated using KGF either systemically, or topically if the drug could be applied and absorbed through the scalp, or by spray injection into the scalp using an air gun or similar technologies. A standard in vivo model of male-pattern baldness which permits the predictive testing of compounds having human therapeutic efficacy is well-known. [Uno, "The Stumptailed Macaque as a Model for Baldness: effects of Minoxidil", *International Journal of Cosmetic Science,* 8:63-71 (1986); Porter R., "Mouse models for human hair loss disorders" J Anat. 202: 125-31 (2003)].

Studies have shown that administration of KGF could induce cell growth in the gastrointestinal tract [Playford et al., *J Pathol.* 184:316-22, (1998)]. Gastric ulcers, although treatable by H2 antagonists, cause significant morbidity and a recurrence rate, and heal by scar formation of the mucosal lining. The ability to regenerate glandular mucosa more rapidly in patients with gastric ulcers, e.g., by treatment with KGF, would offer a significant therapeutic improvement in the treatment of gastric ulcers. Standard in vivo models of gastric ulcers which permit the predictive testing of compounds having human therapeutic efficacy are well-known, for example, Tarnawski, et al., ["Indomethacin Impairs Quality of Experimental Gastric Ulcer Healing: A Quantitative Histological and Ultrastructural Analysis", In: Mechanisms of Injury, Protection and Repair of the Upper Gastrointestinal Tract, (eds) Garner and O'Brien, Wiley & Sons (1991); and Astudillo et al., ["Gastroprotective activity of oleanolic acid derivatives on experimentally induced gastric lesions in rats and mice" *J Pharm Pharmacol.* 54:583-8 (2002)].

Duodenal ulcers, like gastric ulcers, are treatable, but the development of a therapeutic agent to more fully and more rapidly regenerate the mucosal lining of the duodenum would be an important advance. In addition, a therapeutic agent to regeneratively heal these ulcers and decrease their recurrence would be of benefit. KGF offers such potential. Standard in vivo models of duodenal ulcers which permit the predictive testing of compounds having human therapeutic efficacy are well-known [Berg, et al., "Duodenal ulcers produced on a diet deficient in pantothenic acid", *Proc. Soc. Exp. Biol. Med.,* 7:374-376 (1949); Szabo and Pihan, "Development and Significance of Cysteamine and Propionitrile Models of Duodenal Ulcer", *Chronobiol. Int.,* 6:31-42 (1987); Robert, et al., "Production of Secretatogues of Duodenal Ulcers in the Rat", *Gastroenterology,* 59:95-102 (1970); and Keshavarzian et al., "Gastroduodenal ulcers in rats induced by 1-methyl-4-phenyl-1,2,5,6-tetrahydropyridine (MPTP): requirement for gastric acid secretion and the role of prostaglandins" *Res Commun Chem Pathol Pharmacol.* 70:21-48 (1990)].

Erosions of the stomach and esophagus, like erosive gastritis, esophagitis, or esophageal reflux, are treatable but the development of a therapeutic agent to more fully and rapidly regenerate the mucosal lining of the stomach and esophagus would be an important advance. In addition, a therapeutic agent to regeneratively heal these erosions and decrease their recurrence would be of benefit. KGF offers such potential. Standard in vivo models of erosion of the stomach and esophagus, like erosive gastritis, esophagitis, or esophageal reflux, which permit the predictive testing of compounds having human therapeutic efficacy are well-known [Geisinger et al, "The histologic development of acid-induced esophagitis in the cat", *Mod-Pathol.,* 3:619-624 (1990); Carlborg et al., "Tetracycline induced esophageal ulcers. A clinical and experimental study", *Laryngoscope,* 93:184-187 (1983); Carlborg et al., "Esophageal lesions caused by orally administered drugs. An experimental study in the cat", Eur-Surg-Ethanol on esophageal motility in cats, *Alcohol-Clin-Exp-Res.*, 15:116-121 (1991), and Katz et al., "Acid-induced esophophagitis in cats is prevented by sucralfate but not synthetic prostaglandin E.", *Dig-Dis-Sci.*, 33:217-224 (1988)].

Inflammatory bowel diseases, such a Crohn's disease (affecting primarily the small intestine) and ulcerative colitis (affecting primarily the large bowel), are chronic diseases of unknown etiology which result in the destruction of the mucosal surface, inflammation, scar and adhesion formation during repair, and significant morbidity to the affected individuals. Therapy at present is designed to control the inflammation, however, KGF treatment has been shown to induce proliferation of gastrointestinal tract epithelium in IBD affected animals [Housley et al., *J Clin Invest.* 94:1764-77, (1994)]. A therapeutic such as KGF to stimulate resurfacing of the mucosal surface, resulting in faster healing, may be of benefit in controlling progression of disease. Standard in vivo models of inflammatory bowel disease which permit the predictive testing of compounds having human therapeutic efficacy are well-known. [Morris, et al., "Hapten-induced Models of Chronic Inflammation and Ulceration in the Rat Colon", *Gastroenterology,* 96:795-803 (1989); Rachmilewitz, et al., "Inflammatory Mediators of Experimental Colitis in Rats", *Gastroenterology,* 97:326-327 (1989); Allgayer, et al., "Treatment with 16,16'-dimethyl-prostaglandin E2 before and after induction of colitis with trinitrobenzene-sulfonic acid in Rats", *Gastroenterology,* 96:1290-1300 (1989); "Review: Experimental Colitis in Animal Models", *Scand. J Gastroenterol,* 27:529-537 (1992)].

Hyaline membrane disease of premature infants results in the absence of surfactant production by type II pneumocytes within the lung, resulting in the collapse of the alveoli. Hyaline membrane disease may have both acute and chronic phases. The acute phase of hyaline membrane disease (Infant Respiratory Distress Syndrome—IRDS) is treated with mechanical ventilation and treatment with 80-100% concentrations of supplemental oxygen and by administration of an exogenous surfactant. Those patients undergoing a prolonged course of treatment may develop the chronic disease phase of hyaline membrane disease (bronchopulmonary dysplasia—BPD). While the surfactants have greatly reduced the mortality associated with IRDS, the morbidity associated with BPD remains high. Thus, there is a need to develop effective treatments to accelerate maturation of the lung and secretion of surfactant in neonates to reduce the incidence of BPD. Although corticosteroids can accelerate maturation and secretion in fetuses twenty-eight weeks old and beyond to a large extent, there is presently no treatment for younger fetuses, resulting in significant morbidity and mortality in this population. The history of BPD suggests that improvements in treatment of IRDS will be matched by mechanical ventilation of even smaller prematurely-born infants and a subsequent increase in the incidence of BPD in these smaller infants. A therapeutic agent such as KGF which would induce proliferation and differentiation of type II pneumocytes [Yi et al., *Inflammation* 22:315-25 (1998)] would be of considerable benefit in the treatment of this disease. Standard in vivo models of IRDS which permit the predictive testing of compounds having human therapeutic efficacy are well-known. Seider, et al., "Effects of antenatal thyrotropin-releasing hormone, antenatal corticosteroids, and postnatal ventilation on surfactant mobilization in premature rabbits", *Am. J. Obstet. Gynec.,* 166:1551-1559 (1992); Ikegami, et al., "Corticosteroid and thyrotropin-releasing hormone effects on preterm sheep lung function", *J. Appl. Physiol.,* 70:2268-2278 (1991). Standard in vivo models of BPD which permit the predictive testing of compounds having human therapeutic efficacy are well-known [Yuh-Chin, et al., "Natural surfactant and hyperoxide lung injury in primates I. Physiology and biochemistry", *J. Appl. Physiol.* 76:991-1001 (1994); and Galan, et al., "Surfactant replacement therapy in utero for prevention of hyaline membrane disease in the preterm baboon", *Am. J. Obstet. Gynecol.,* 169:817-824 (1993)].

Smoke inhalation is a significant cause of morbidity and mortality in the week following a burn injury, due to necrosis of the bronchiolar epithelium and the alveoli. A growth factor such as KGF which could stimulate proliferation and differentiation of these structures, and induce their repair and regeneration, would be of benefit in treating inhalation injuries. A standard in vivo model of smoke inhalation which permits the predictive testing of compounds having human therapeutic efficacy is well-known. Hubbard, et al., "Smoke inhalation injury in sheep", *Am. J. Pathol.,* 133:660-663 (1988).

Emphysema results from the progressive loss of alveoli. A growth factor such as KGF which could stimulate re-growth or, which is cytoprotective for remaining alveoli [Kaza et al., *Circulation.* 106(12 Suppl 1):1120-4 (2002)], would be of therapeutic benefit. At present, no effective treatment is available. A standard in vivo model of emphysema which permits the predictive testing of compounds having human therapeutic efficacy is well-known [Stolk et al., "Induction of emphysema and bronchial mucus cell hyperplasia by intratracheal instillation of lipopolysaccharide in the hamster." *J. Pathol.,* 167:349-56 (1992)].

Hepatic cirrhosis, secondary to viral hepatitis and chronic alcohol ingestion, is a significant cause of morbidity and mortality. Cytoprotection, proliferation, and differentiation of hepatocytes such as by the use of KGF [Danilenki, D., *Toxicol Pathol.* 27:64-71 (1999)] to increase liver function would be of benefit to slow or prevent the development of cirrhosis. A standard in vivo model of hepatic cirrhosis which permits the predictive testing of compounds having human therapeutic efficacy is well-known [Tomaszewski, et al., "The production of hepatic cirrhosis in rats", *J. Appl. Toxicol.,* 11:229-231 (1991)].

Fulminant liver failure is a life-threatening condition which occurs with endstage cirrhosis. An agent such as KGF which could induce proliferation of remaining hepatocytes would be of direct benefit to this disease, which is presently treatable only with liver transplantation. Standard in vivo models of fulminant liver failure which permit the predictive testing of compounds having human therapeutic efficacy are well-known [Mitchell, et al., "Acetaminophen-induced hepatic necrosis I. Role of drug metabolism", *J. Pharmcol. Exp. Ther.,* 187:185-194 (1973); and Thakore and Mehendale, "Role of hepatocellular regeneration in CC14 autoprotection", *Toxicologic Pathol.* 19:47-58 (1991)].

Acute viral hepatitis is frequently subclinical and self-limiting. However, in a minority of patients, severe liver damage can result over several weeks. A cytoprotective agent such as KGF would be of use in preventing hepatocellular degeneration.

Toxic insults to the liver caused by acetaminophen, halothane, carbon tetrachloride, and other toxins could be ameliorated by a growth factor (KGF) which is cytoprotective for hepatocytes. Standard in vivo models of liver toxicity which permit the predictive testing of compounds having human therapeutic efficacy are well-known [Mitchell, et al. (1973), supra, and Thakore and Mehendale (1991), supra)].

Graft-versus-host disease (GVHD) (chronic or acute) is a leading cause of ineffective bone marrow or hematopeitic cell transplant in patients. GVHD leads to damage of several organ systems due to upregulation of immunomodulatory and cytotoxic factors. GVHD results in damage to multiple areas including the gastrointestinal tract, the lung, the liver, the skin, and the mucous glands in the eyes, salivary glands in the mouth, and glands that lubricate the stomach lining and intestines. Recent studies in animals induced with GVHD indicate that rHuKGF-treated recipients did not develop intestinal GVHD, did not develop endotoxemia, and did not die [Panoskaltsis-Mortari et al., "Keratinocyte growth factor facilitates alloengraftment and ameliorates graft-versus-host disease in mice by a mechanism independent of repair of conditioning-induced tissue injury" *Blood.* 96:4350-6 (2000)]. These data suggest that KGF prevents the development of acute lethal GVHD by protecting epithelial cell injury mediated by TNF-alpha, NO, and other potential cytotoxic factors. An agent such as KGF which could induce proliferation of epithelia in many of these cells types would be of direct benefit to in treating GVHD in human transplant recipients.

Formulations and Administration

KGF proteins or peptides are useful for use in pharmaceutical formulations in order to treat human diseases as described above. KGF may be prepared as a liquid or a lyophilized formulation. In a preferred embodiment the KGF compositions are lyophilized. Lyophilization may be carried out using techniques common in the art and should be optimized for the composition being developed [Tang et al., *Pharm Res.* 21:191-200, (2004) and Chang et al., *Pharm Res.* 13:243-9 (1996)].

A lyophilization cycle is usually composed of three steps: freezing, primary drying, and secondary drying [A. P. Mackenzie, *Phil Trans R Soc London, Ser B, Biol* 278:167 (1977)]. In the freezing step, the solution is cooled to initiate ice formation and completion. Furthermore, this step induces the crystallization of the bulking agent. The ice sublimes in the primary drying stage, which is conducted by reducing chamber pressure below the vapor pressure of the ice, using a vacuum and introducing heat to promote sublimation. Finally, adsorbed or bound water is removed at the secondary drying stage under reduced chamber pressure and an elevated shelf temperature. The process produces a material known as a lyophilized cake. Thereafter the cake can be reconstituted with either sterile water for injection or an appropriate multi dose reconstitution solution prior to use.

The lyophilization cycle not only determines the final physical state of the excipients but also affects other parameters such as reconstitution time, appearance, stability and final moisture content. The composition structure in the frozen state proceeds through several transitions (e.g., glass transitions and crystallizations) that occur at specific temperatures and can be used to understand and optimize the lyophilization process. The glass transition temperature (Tg) can provide information about the physical state of a solute and can be determined by differential scanning calorimetry (DSC). This is an important parameter that must be taken into account when designing the lyophilization cycle. Furthermore, in the dried state, the glass transition temperature provides information on the storage temperature of the final product.

In a particular embodiment of the present compositions, a stabilizer is added to the lyophilization formulation to prevent or reduce lyophilization induced or storage induced aggregation and chemical degradation. A hazy or turbid solution upon reconstitution indicates that the protein has precipitated. The term "stabilizer" means an excipient capable of preventing aggregation or other physical degradation, as well as chemical degradation (for example, autolysis, deamidation, oxidation, etc.) in an aqueous and solid state. Stabilizers that are conventionally employed in pharmaceutical compositions, including, but not limited to, sucrose, trehalose or glycine, may be used [Carpenter et al., *Develop. Biol. Standard* 74:225, (1991)]. Surfactant stabilizers, such as polysorbate 20 (Tween 20) or polysorbate 80 (Tween 80), may also be added in appropriate amounts to prevent surface related aggregation phenomenon during freezing and drying [Chang, B, *J. Pharm. Sci.* 85:1325, (1996)]. If desired, the lyophilized compositions also include appropriate amounts of bulking and osmolarity regulating agents suitable for forming a lyophilized "cake". Bulking agents may be either crystalline (for example, mannitol, glycine) or amorphous (for example, sucrose, polymers such as dextran, polyvinylpyrolidone, carboxymethylcellulose. In one embodiment, the bulking agent is mannitol. In a further embodiment, mannitol is incorporated in a concentration of about 2% to about 5% w/v, and in a yet further embodiment in a concentration of about 3% to 4.5% w/v, to produce a mechanically and pharmaceutically stable and elegant cake. In another embodiment, the mannitol concentration is 2% w/v.

The choice of a pharmaceutically-acceptable buffer and pH has also been found to affect the stability of the present compositions. The buffer system present in the compositions is selected to be physiologically compatible and to maintain a desired pH in the reconstituted solution as well as in the solution before lyophilization. Preferably, the buffers have a pH buffering capacity in the range of from about pH 6.0 to about pH 8.0. A series of screening studies incorporating the above mentioned parameters are typically performed to select the most stable formulation condition.

The compositions are expected to be stable for at least two years at 2° C. to 8° C. in the lyophilized state. This long-term stability is beneficial for extending the shelf life of the pharmaceutical product.

The present invention further contemplates methods for the preparation of the present KGF formulations. In one aspect, methods for preparing a lyophilized KGF formulation comprising the steps of:

(a) mixing said KGF composition in a buffer comprising histidine, a bulking agent, a sugar and a surfactant;

(b) lyophilizing said KGF.

The present methods further comprise one or more of the following steps: adding a stabilizing agent to said mixture prior to lyophilizing, adding at least one agent selected from a bulking agent and an osmolarity regulating agent, and a surfactant to said mixture prior to lyophilization. The bulking agent may be any bulking agent set forth above. Preferably, the bulking agent is mannitol. The sugar may be any stabilizing sugar set out above. In one embodiment, the stabilizing agent is sucrose. The surfactant may be any surfactant set out above. In one embodiment, the surfactant is polysorbate 20.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration [Chen, *Drug Development and Industrial Pharmacy,* 18:1311-1354 (1992)].

The lyophilized KGF composition may be reconstituted as an aqueous solution. A variety of aqueous carriers, e.g., sterile water for injection, water with preservatives for multi dose use, or water with appropriate amounts of surfactants (for example, polysorbate 20), 0.4% saline, 0.3% glycine, or aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

To administer compositions of the invention to human or test animals, it is preferable to formulate the compositions in a composition comprising one or more pharmaceutically acceptable carriers. The phrases "pharmaceutically" or "pharmacologically acceptable" refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

The keratinocyte growth factor compositions may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Kits

As an additional aspect, the invention includes kits which comprise one or more compounds or compositions packaged in a manner which facilitates their use for administration to subjects. In one embodiment, such a kit includes a compound or composition described herein (e.g., a composition comprising a keratinocyte growth factor), packaged in a container such as a sealed bottle or vessel, with a label affixed to the container or included in the package that describes use of the compound or composition in practicing the method. In one embodiment, the kit contains a first container having a lyophilized keratinocyte growth factor composition and a second container having a physiologically acceptable reconstitution solution for the lyophilized composition. Preferably, the compound or composition is packaged in a unit dosage form. The kit may further include a device suitable for administering the composition according to a specific route of administration. Preferably, the kit contains a label that describes use of the keratinocyte growth factor composition.

Additional aspects and details of the invention will be apparent from the following examples.

Example 1

Liquid Formulation OF KGF

Product stability, shelf-life and bioactivity are important aspects to any therapeutically effective composition. Designing and formulating compositions that are stable when stored at recommended storage temperatures for extended periods of time, but retain significant biological activity are key elements to pharmaceutical compositions.

In previous experiments, liquid formulations of KGF showed significant aggregation and subsequent loss of protein at elevated temperatures (37° C.). In order to determine the pH that provided the greatest stability to the KGF compositions, the pH of the liquid formulation of keratinocyte growth factor was tested over a pH range of 3.0 to 9.0.

The KGF used in the following experiments, e.g., Examples 1-3, was the $\Delta$N23 KGF molecule. The pH of the solution was adjusted using either concentrated HCl or sodium hydroxide. Samples of KGF formulation (0.5 mg/ml, 10 mM buffer, 0.1M NaCl) at differing pH were taken at time 0, 6 and 28 hours after incubation at 37° C. (FIG. 1). Percent of recovered protein was measured by SE-HPLC (FIG. 1A) or by CE-HPLC (FIG. 1B). For size-exclusion HPLC (SE-HPLC), samples (40 µg) were loaded onto a G2000SWx1 column (7.8 mm×30 cm) connected to a HP 1090/1050 machine. The protein was eluted using 20 mM sodium phosphate (NaP), 1M NaCl at pH 7.0. Protein was monitored by absorbance at 215 nm. A monomeric peak indicates that there are few aggregates in the KGF formulation.

Cation-exchange (CE)-HPLC was performed on an HP 1090/1050 machine equipped with a Mono-S column at room temperature. 40 µg KGF protein was loaded onto the column and eluted using 20 mM sodium phosphate buffer, pH 8.0, and a salt gradient (1M NaCl). The eluted protein was monitored by absorbance at 215 nm.

Reversed-phase HPLC (RP-HPLC) was performed on an HP 1090/1050 machine using a C4 column from Vydac, (4.6×250 mm) pore size 300 Å. Protein (30 µg) was injected onto the column and eluted using an acetonitrile (ACN) gradient with 0.1% trifluoroacetic acid (TFA) (v/v) and 90% ACN, 0.1% TFA in water (v/v). Protein peaks were monitored by absorbance at 215 nm.

Complete recovery of protein was observed at time 0 over the pH 5.0 to 9.0 range. However, at pH 3.0 complete loss of protein was observed, and pH 4.0 resulted in approximately an 80% loss of the protein due to immediate precipitation. After 6 hours at 37° C., no soluble protein was obtained from the pH 4.0 samples. The percent protein recovered after 28 hours at 37° C. when the soluble KGF was formulated at pH 5 to 9 was less than 20%. However, at pH 7.0 only 20% of total protein was lost. The loss in soluble protein after 28 hours at 37° C. was primarily due to aggregation.

These results indicate that the KGF protein in liquid formulations is most stable at neutral pH, however even in this optimal pH range, keeping KGF as a liquid results in significant loss of protein due to aggregation.

Example 2

Formulation of KGF Composition for Lyophilization

In order to develop a more stable KGF composition, it was decided to formulate KGF as a lyophilized product. Previous attempts at formulating a lyophilized KGF composition involved manipulation of the reconstitution solution, resulting in a composition that produced fewer protein aggregates depending on the composition of the reconstitution solution [Zhang et al., *Pharm. Res.* 12:1447-52 (1995)]. However, in this previous study, any aggregation seen during reconstitution was very difficult or impossible to reverse.

This example describes lyophilizing the protein in a solution that will prevent aggregation upon reconstitution independent of the reconstitution solution, to eliminate the need for a custom reconstitution solution.

To determine the composition of a stable lyophilization formulation, KGF, e.g., ΔN23 KGF, was lyophilized under varied conditions, altering parameters such as pH, bulking agent, sugar concentration, and surfactant concentration. The long term storage stability of KGF was then determined at the recommended storage temperature.

Lyophilization Cycle

For lyophilization, samples were loaded into a VirTis Genesis 12 EL pilot scale (VirTis, Gardiner, N.Y.) lyophilizer that was pre-cooled to a chamber temperature of approximately 4° C. Samples were frozen rapidly (about 1° C./minute to −50° C.) and held at that temperature for at least 2 hours. Once samples were placed in the lyophilizer, the shelf temperature was lowered to −50° C. at a rate of approximately 27° C./hour. Samples were held at −50° C. for 2 hours to ensure complete freezing. In an optional step to crystallize mannitol, the shelf temperature was raised to −25° C. at a rate of 10° C./hour, equilibrating for 2-3 hours, and then cooling to −55° C. at a rate of 9° C./hour. After an additional hold of at least 2 hours, a vacuum of approximately 100 mTorr was applied. The shelf temperature was raised to −35° C. for primary drying, but may be within the range of −45° C. to −10° C. Primary drying was continued for 40 hours, but may be within the range of 24-48 hours. The shelf temperature was then raised to +20° C. to +25° C. at a rate of 5° C./hour for secondary drying, and vacuum was lowered to approximately 50 mTorr). Secondary drying was performed for 36 hours, but may be performed for anywhere from 24-72 hours. At the conclusion of secondary drying, the samples were stoppered under vacuum (≦25 mTorr) and vials removed from the freeze dryer. Vials were crimp capped and placed at various temperatures for stability testing.

Effect of pH on the Stability of Lyophilized KGF

The stability of KGF over a range of pH values was first assessed. KGF (5 mg/ml) was formulated in a solution comprising 10 mM histidine, 3% mannitol, 2% sucrose and 0.01% polysorbate 20 at either pH 6.0, pH 6.5 or pH 7.0. SE-HPLC of the pre-lyophilized sample demonstrated a percent main peak of 99%, which corresponds to 99% monomeric active component.

In order to perform accelerated stability studies, some samples were transferred to incubators for storage. Other samples were transferred to a −70° C. freezer to serve as controls. The bulk of the vials were stored at 4° C. At the time of analysis, samples were reconstituted with 1.2 mL sterile water for injection (WFI).

SE-HPLC of the lyophilized KGF samples after storage for 6 months at 45° C. demonstrated that the percent main peak of the samples at all pHs tested was approximately 97.5%, indicating that in the pH range of 6.0 to 7.0 the lyophilized KGF composition is stable after 6 months storage at high temperature. These studies also indicated that the pH range of 5.0 to 8.0 provided stable protein when the formulation was kept at 4° C.

Effect of Sucrose Concentration on Stability of KGF

To assess the amount of sucrose that provided the greatest stability to the lyophilized KGF, recombinant human KGF (1 mg/ml) was formulated in a composition comprising 10 mM histidine, 3% mannitol, at pH 7.0 in a solution either lacking sucrose or with 2% sucrose (w/v). The samples were lyophilized as above and allowed to incubate up to 3 months at 45° C.

SE-HPLC measurement of the percent main peak of KGF formulations with and without sucrose indicates that the addition of 2% sucrose provides a significant stability to the lyophilized KGF formulation. KGF lyophilized with 2% sucrose demonstrated approximately 99.5% main peak immediately post-lyophilization, and 98.5% at both 1 month and 3 months post lyophilization. The formulations lacking sucrose exhibited approximately 96% main peak and approximately 93.5% main peak at 1 month and 3 months post-lyophilization, respectively.

These results indicate that in formulations without sucrose, the percent active monomer peak decreased 7% after storage for 3 months at 45° C., while there was only a small decrease in monomer peak in formulations having sucrose. Thus, sucrose acts as a potent stabilizer to the KGF when added to the lyophilized formulation.

Further analysis was performed using KGF lyphilization product comprising 10 mM histidine, pH 6.5, over a range of sucrose concentrations between 1% and 3% sucrose, wherein the solution always maintained isotonicity with the appropriate percent of mannitol. Lyophilization product having 1%-3% sucrose and stored at 37° C. for one year showed protein stability comparable to formulations with 2% sucrose, with the percent main peak remaining above 99% for all formulations tested.

Effects of Polysorbate 20 Concentration on the Stability of KGF

The concentration of polysorbate 20 in the lyophilized formulation for KGF was selected based on its ability to eliminate particle formation upon reconstitution. Recombinant human KGF was formulated in a composition comprising 10 mM histidine, 3% mannitol, 2% sucrose at pH 7.0 and lyophilized. KGF was then reconstituted in a solution containing varying concentrations of polysorbate 20. The lyophilized cake consisted of 5 mg/ml KGF formulated as above. Table 1 describes the recorded observations of the lyophilized formulation upon reconstitution.

TABLE 1

| Diluent in reconstitution solution | Visual observations after reconstitution |
| --- | --- |
| 0.1% polysorbate 20 | Clear but foams |
| 0.01% polysorbate 20 | Clear |
| 0.004% polysorbate 20 | Few particulates/borderline |
| 0.001% polysorbate 20 | Particulates |
| water | Particulates |

Further studies showed that the formulation with polysorbate 20 included in the cake prior to lyophilization was equally stable after 4 months at 45° C. when compared to the addition of polysorbate 20 in the reconstitution solution. SE-HPLC analysis [Biorad Biosil SEC 125 (7.8 mm×30 cm), 20 mM NaP, pH 7.0, 1M NaCl, 40 µg injection load] showed that the loss of monomeric KGF was negligible for all polysorbate concentrations tested (as in Table 1) at 0, 1 and 4 months. A concentration of 0.01% (w/v) was selected for inclusion in the formulation based on its ability to consistently eliminate visible particles upon reconstitution.

Effect of Mannitol Concentration on the stability of KGF

Mannitol and other bulking agents are included in formulations to obtain good cake appearance and quality. In addition, they help to maintain the isotonicity of the pharmaceutical composition with physiological fluid. For example, physiological fluid has an osmolarity of 290-320 mOsm. The mannitol concentration in the final KGF formulation was adjusted to be iso-osmotic with physiological fluid.

To assess the percent mannitol concentration that provides protein stability in the lyophilization formulation, KGF at 3 mg/ml was lyophilized in a formulation comprising 10 mM histidine, 2% sucrose, and 0.01% polysorbate 20 at pH 7.0, and either 3% mannitol or 4% mannitol. The KGF formulations were lyophilized and stored for 1 year at 4° C. Osmolarity was measured using an Osmometer Model 3D3 from Advanced Instruments (Norwood, Mass.). The measured osmolarity for the 4% mannitol solution was 312 mOsm while the 3% mannitol formulation resulted in a solution of 250 mOsm.

FIG. 2 shows an overlay of the reversed-phase (RP-HPLC) chromatograms of the isotonic 4% mannitol/2% sucrose formulation compared with the slightly hypotonic 3% mannitol/2% sucrose formulation taken at time zero (FIG. 2A) or after 1 year of storage at 4° C. (FIG. 2B). The results demonstrate that the iso-osmotic formulation is stable after 1 year at the recommended storage temperature of 2° to 8° C. In addition, the cake appearance for the iso-osmotic formulation was also good and its moisture content was less than 2%. Based on this study, 4% mannitol was recommended for use in the lyophilized formulation.

Effect of Protein Concentration on Stability of rHuKGF

Protein concentration in the lyophilized sample can also have an effect on the stability of the lyophilization quality of the protein as well as the stability of the reconstituted product.

The effect of KGF concentration on stability was explored at 0.5, 1, 2, 3 and 5 mg/ml. Samples were formulated and lyophilized in 10 mM histidine, 3% mannitol, 2% sucrose and 0.005% polysorbate 20 at pH 6.5. The lyophilized samples were stored for 24 weeks at 45° C. before reconstitution. Protein degradation was monitored by SE-HPLC, RP-HPLC, CE-HPLC and SDS-PAGE. For this experiment, SE-HPLC was performed as above using the HP system and a G2000SWx1 column.

Figure 3:
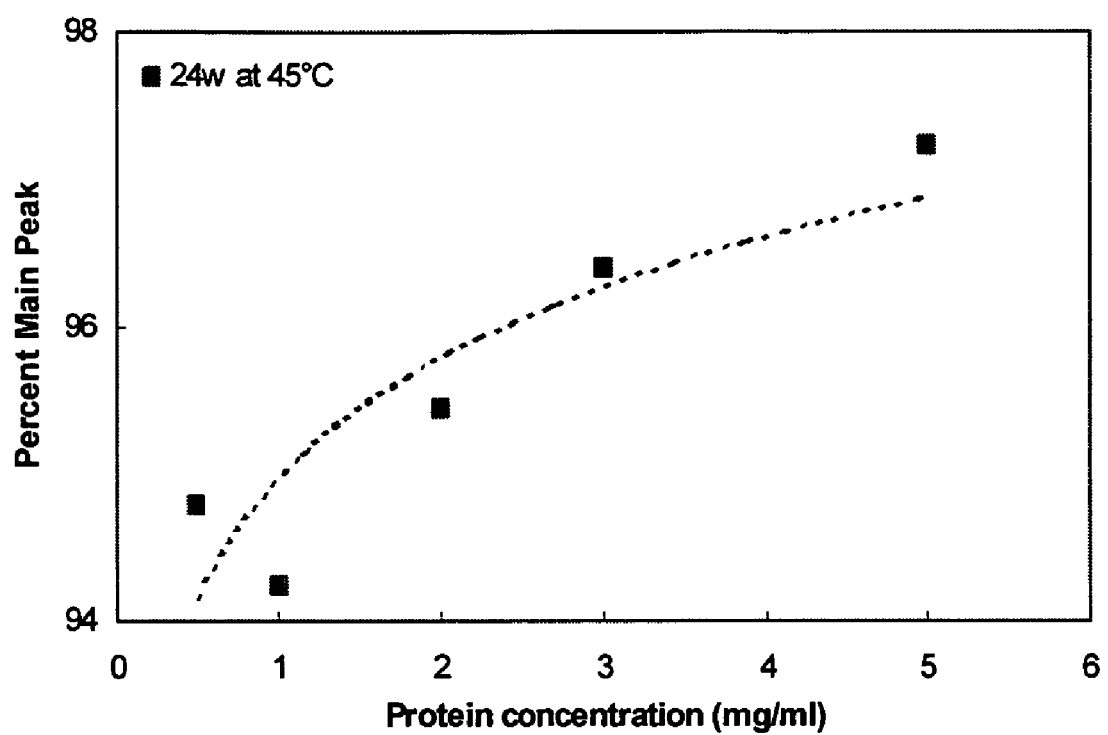
FIG. 3 represents the percent main peak as a function of protein concentration from an SE-HPLC analysis of lyophilized KGF formulations after storage for 24 weeks at 45° C.

FIG. 3 represents the percent main peak as a function of protein concentration from an SE-HPLC analysis of KGF after storage for 24 weeks at 45° C. The dashed line represents a trend line to the measured data. Based on SE-HPLC data, stability increased as the concentration of KGF increased, at least up to a concentration of 5 mg/ml. The dependence of the percent main peak on protein concentrations as determined by RP-HPLC and CE-HPLC are similar to that seen with SE-HPLC. Further studies indicated that a protein concentration of 15 mg/mL also resulted in stable lyophilized formulations.

An optimized KGF lyophilization formulation comprising 10 mM histidine, 0.01% polysorbate 20, 2% sucrose and 3% mannitol at pH 6.5 was stored for over 4 years at 2° to 8° C. Upon reconstitution, the KGF formulation was shown to maintain KGF activity as tested below, indicating that the particular composition maintained the type of stability and activity necessary for a therapeutically effective pharmaceutical composition.

Example 3

Bioassay of the Reconstituted KGF Formulation

One of the factors in formulation of a pharmaceutically effective product is the requirement for high biological activity of the protein of interest.

The bioactivity of the KGF, e.g., ΔN23 KGF, formulations were tested using 32D KECA clone 16 cells, which are IL-3 dependent murine lymphoblast cells that proliferate in the presence of KGF, similar to 32D clone 3 cells (ATCC# CRL-11346), and are a useful proliferation assay system, as described in Hsu et al., 1999 Biochemistry, 38, 2523-2534.

32D clone 16 cells are maintained in growth medium [RPMI, Fetal bovine serum (10%)(Hyclone, Logan, Utah), glutamine (1%) (Gibco/Invitrogen, Carlsbad, Calif.), geneticin (2%) (Gibco), and murine IL-3 (12 ng/mL)(Biosource International, Camarillo, Calif.)] at 37° C. and 5.5% $CO_2$. Sample KGF formulations or reference standard (ΔN23 KGF stored lyophilized at −70° C.) are reconstituted in assay medium [RPMI, FBS (6%), glutamine(1%), heparin (0.6 µg/ml)(Sigma, St. Louis, Mo.)] to approximately 25 ng/mL. Serial dilutions are then made to obtain a range of concentrations from approximately 25 ng/mL to 1.6 ng/mL.

To test the bioactivity of the KGF formulation, the 32D clone 16 cells are plated in 150 µL at $2.0 \times 10^5$ cell/mL. Reference standard, control and KGF test samples at the desired concentration were added to the sample wells in a 50 µL volume. Plates of cells and sample were incubated approximately 24 hours at 37° C. and 5.5% $CO_2$. On day 2, 40 µL of Alomar Blue (AccuMed International, Chicago, Ill.) was added to all wells and mixed. The plates were incubated for another 24 hours at 37° C. and 5.5% $CO_2$. After 24 hours, fluorescence was measured on a Fluorescence Reader (Cytofluor II or Cytofluor Series 4000, PerSeptive Biosystems, Framingham, Mass.) using an excitation wavelength of 530-560 nm and an emission wavelength of 590 nm.

Lyophilized KGF formulations from 3 reconstituted lots stored at 2° to 8° C. for 7 days demonstrated similar bioactivity as the reference standard KGF protein (stored lyophilized at −70° C.), exhibiting ≥100% bioactivity at day 0, and 92%, 100% and 107% activity, respectively, at day 7. KGF formulations stored at 25° C. showed ≥100% bioactivity at time 0, which decreased slightly after 4 hours to 90%, 95% and 100% bioactivity, respectively, compared to native KGF. This level of activity was also maintained after storage of reconstituted KGF formulation at 25° C. for 24 hours, indicating the stability of the KGF formulations.

These results indicate that the reconstituted KGF formulations described herein are as potent as the reference standard KGF protein and the formulation has no deleterious effects on the stability or potency of KGF, e.g., ΔN23KGF, and are thus useful as therapies in the treatment of individuals to promote growth of epithelial cells and the like.

In addition, KGF bioactivity can be assessed by the ability of the reconstituted formulations to promote growth of Balb/C-MK cells. Stock cultures of Balb/MK cells are grown and maintained in low calcium Dulbecco's modified Eagle medium supplemented with 10% fetal bovine serum, 0.25 µg/ml fungizone, and 10 ng/ml aPGF. The cells are incubated at 37° C. in a 10% $CO_2$ atmosphere with 99% humidity. For the bioactivity assay, the cells are seeded in 12-well plates at a density of $5 \times 10^3$ cells per well in 1 ml of medium as described in Gospodarowicz et al. [*J. Cell. Physiol.* 142:325-333 (1990)]. A predetermined amount of KGF formulation is added to the cell culture well. FGF is used as a positive control.

After five days in culture, the cells are trypsinized and the final cell density determined using a cell counter. The cells are released from the plates by replacing the culture medium with a solution containing 0.9% NaCl, 0.01M sodium phosphate (pH 7.4), 0.05% trypsin, and 0.02% EDTA (STV) and incubated for 5-10 minutes at 37° C., and then the stock culture medium is added to the cells.

An increase in Balb/C-MK cell population in the KGF treated sample compared to the untreated cells shows that the KGF composition does not lose its bio-activity during the formulation process and indicates that the KGF formulation provides an effective therapeutic agent to treat subjects in need of increased KGF activity.

Numerous modifications and variations in the invention as set forth in the above illustrative examples are expected to occur to those skilled in the art. Consequently only such limitations as appear in the appended claims should be placed on the invention.

We claim:

1. A lyophilized composition comprising a keratinocyte growth factor (KGF), histidine, mannitol, sucrose, and polysorbate 20, wherein reconstitution of the lyophilized composition with water yields a reconstituted solution having a pH of about 6.5 and comprising about 10 mM histidine, about 4% mannitol, about 2% sucrose, and about 0.01% (w/v) polysorbate 20, and wherein the KGF stimulates keratinocyte proliferation and comprises the amino acid sequence of SEQ ID NO: 2 or a variant thereof selected from the group consisting of SEQ ID NO: 3 (ΔN23), ΔN15, ΔN16, ΔN18, ΔN24, ΔN25, ΔN26, ΔN27, C(1,15)S, ΔN3/C(15)S, ΔN3/C(15)-, ΔN8/C(15)S, ΔN8/C(15)-, C(1,15)S/R(144)E, C(I,15)S/R(144)Q, ΔN23/R(144)Q, C(I,15,40)S, C(1,15,102)S, C(I, 15,102,106)S, ΔN23/N(137)E, ΔN23/K(139)E, ΔN23/K(139)Q, ΔN23/R(144)A, ΔN23/R(144)E, ΔN23/R(144)L, ΔN23/K(147)E, ΔN23/K(147)Q, ΔN23/K(153)E, ΔN23/K(153)Q, ΔN23/Q(152)E/K(153)E, R(144)Q, and H(116)G.

2. The composition of claim 1 wherein the KGF comprises the amino acid sequence of SEQ ID NO:2.

3. The composition of claim 1 wherein the KGF comprises the amino acid sequence of SEQ ID NO: 3 (ΔN23).

4. The composition of claim 1 wherein the KGF concentration in the reconstituted solution is between 3 mg/mL and 15 mg/mL.

5. The composition of claim 4 wherein the KGF in the reconstituted solution concentration is about 5 mg/mL.

6. A lyophilized composition comprising a keratinocyte growth factor (KGF), histidine, mannitol, sucrose, and polysorbate 20, wherein reconstitution of the lyophilized composition with water yields a reconstituted solution having a pH of about 6.5 and comprising about 5 mg/mL KGF, about 10 mM histidine, about 4% mannitol, about 2% sucrose, and about 0.01% (w/v) polysorbate 20, and wherein the KGF consists of the amino acid sequence of SEQ ID NO: 3 (ΔN23).

7. A method for making a lyophilized keratinocyte growth factor (KGF) comprising the steps of
a) preparing a solution having a pH of about 6.5 and comprising a KGF, about 10 mM histidine, about 4% mannitol, about 2% sucrose, and about 0.01% (w/v) polysorbate 20, wherein the KGF stimulates keratinocyte proliferation and comprises the amino acid sequence of SEQ ID NO: 2 or a variant thereof selected from the group consisting of SEQ ID NO: 3 (ΔN23), ΔN15, ΔN16, ΔN18, ΔN24, ΔN25, ΔN26, ΔN27, C(1,15)S, ΔN3/C(15)S, ΔN3/C(15)-, ΔN8/C(15)S, ΔN8/C(15)-, C(1,15)S/R(144)E, C(I,15)S/R(144)Q, ΔN23/R(144)Q, C(I,15,40)S, C(1,15,102)S, C(I, 15,102,106)S, ΔN23/N(137)E, ΔN23/K(139)E, ΔN23/K(139)Q, ΔN23/R(144)A, ΔN23/R(144)E, ΔN23/R(144)L, ΔN23/K(147)E, ΔN23/K(147)Q, ΔN23/K(153)E, ΔN23/K(153)Q, ΔN23/Q(152)E/K(153)E, R(144)Q and H(116)G; and
b) lyophilizing said solution.

8. The method of claim 7 wherein the KGF comprises the amino acid sequence of SEQ ID NO: 2.

9. The method of claim 7 wherein the KGF comprises the amino acid sequence of SEQ ID NO: 3 (ΔN23).

10. The method of claim 7, wherein the KGF concentration in the reconstituted solution is between 3 mg/mL and 15 mg/mL.

11. The method of claim 10, wherein the KGF concentration in the reconstituted solution is about 5 mg/mL.

12. A kit for preparing an aqueous pharmaceutical composition comprising: a first container having lyophilized composition comprising a keratinocyte growth factor (KGF), histidine, mannitol, sucrose, and polysorbate 20, wherein reconstitution of the lyophilized composition with water yields a reconstituted solution having a pH of about 6.5 and comprising about 10 mM histidine, about 4% mannitol, about 2% sucrose, and about 0.01% (w/v) polysorbate 20, and wherein the KGF stimulates keratinocyte proliferation, and comprises the amino acid sequence of SEQ ID NO: 2 or a variant thereof selected from the group consisting of SEQ ID NO: 3 (ΔN23), ΔN15, ΔN16, ΔN18, ΔN24, ΔN25, ΔN26, ΔN27, C(1,15)S, ΔN3/C(15)S, ΔN3/C(15)-, ΔN8/C(15)S, ΔN8/C(15)-, C(1,15)S/R(144)E, C(I,15)S/R(144)Q, ΔN23/R(144)Q, C(I,15,40)S, C(1,15,102)S, C(I, 15,102,106)S, ΔN23/N(137)E, ΔN23/K(139)E, ΔN23/K(139)Q, ΔN23/R(144)A, ΔN23/R(144)E, ΔN23/R(144)L, ΔN23/K(147)E, ΔN23/K(147)Q, ΔN23/K(153)E, ΔN23/K(153)Q, ΔN23/Q(152)E/K(153)E, R(144)Q and H(116)G; and a second container having a physiologically acceptable solvent for the lyophilized composition.

13. The kit of claim 12 wherein the KGF comprises the amino acid sequence of SEQ ID NO: 2.

14. The kit of claim 12 wherein the KGF comprises the amino acid sequence of SEQ ID NO: 3 (ΔN23).

15. The kit of claim 12, wherein the KGF concentration in the reconstituted solution is between 3 mg/mL and 15 mg/mL.

16. The kit of claim 15, wherein the KGF concentration in the reconstituted solution is about 5 mg/mL.

17. A method for treating a wound comprising administering to a human subject in need thereof an effective amount of a solution having a pH of about 6.5 and comprising a keratinocyte growth factor (KGF), about 10 mM histidine, about 4% mannitol, about 2% sucrose, and about 0.01% (w/v) polysorbate 20, wherein the KGF stimulates keratinocyte proliferation and comprises the amino acid sequence of SEQ ID NO: 2 or a variant thereof selected from the group consisting of SEQ ID NO: 3 (ΔN23), ΔN15, ΔN16, ΔN18, ΔN24, ΔN25, ΔN26, ΔN27, C(1,15)S, ΔN3/C(15)S, ΔN3/C(15)-, ΔN8/C(15)S, ΔN8/C(15)-, C(1,15)S/R(144)E, C(1,15)S/R(144)Q, ΔN23/R(144)Q, C(I,15,40)S, C(1,15,102)S, C(I,15,102,106)S, ΔN23/N(137)E, ΔN23/K(139)E, ΔN23/K(139)Q, ΔN23/R(144)A, ΔN23/R(144)E, ΔN23/R(144)L, ΔN23/K(147)E, ΔN23/K(147)Q, ΔN23/K(153)E, ΔN23/K(153)Q, ΔN23/Q(152)E/K(153)E, R(144)Q, and H(116)G.

18. The method of claim 17, wherein the KGF comprises the amino acid sequence of SEQ ID NO: 3 (ΔN23).

19. A method for treating mucositis comprising administering to a human subject in need thereof an effective amount of a solution having a pH of about 6.5 and comprising a keratinocyte growth factor (KGF), about 10 mM histidine, about 4% mannitol, about 2% sucrose, and about 0.01% (w/v) polysorbate 20, wherein the KGF stimulates keratinocyte proliferation and comprises the amino acid sequence of SEQ ID NO: 2 or a variant thereof selected from the group consisting of SEQ ID NO: 3 (ΔN23), ΔN15, ΔN16, ΔN18, ΔN24, ΔN25, ΔN26, ΔN27, C(1,15)S, ΔN3/C(15)S, ΔN3/C(15)-, Δ8/C(15)S, ΔN8/C(15)-, C(1,15)S/R(144)E, C(I,15)S/R(144)Q, ΔN23/R(144)Q, C(1,15,40)S, C(1,15,102)S, C(I,15,102,106)S, ΔN23/N(137)E, ΔN23/K(139)E, ΔN23/K(139)Q, ΔN23/R(144)A, ΔN23/R(144)E, ΔN23/R(144)L, ΔN23/K(147)E, ΔN23/K(147)Q, ΔN23/K(153)E, ΔN23/K(153)Q, ΔN23/Q(152)E/K(153)E, R(144)Q, and H(116)G.

20. The method of claim 19, wherein the KGF comprises the amino acid sequence of SEQ ID NO: 3 (ΔN23).

\* \* \* \* \*